US006996429B2

(12) United States Patent
Yaksh et al.

(10) Patent No.: US 6,996,429 B2
(45) Date of Patent: Feb. 7, 2006

(54) APPARATUS AND METHOD FOR DETECTING FLINCH RESPONSE TO NOCICEPTIVE AGENTS

(75) Inventors: Tony Yaksh, San Diego, CA (US); George Ozaki, San Diego, CA (US)

(73) Assignee: Regents of the Univeristy of California, San Diego, Oakland, CA (US)

( * ) Notice: Subject to any disclaimer, the term of this patent is extended or adjusted under 35 U.S.C. 154(b) by 200 days.

(21) Appl. No.: 09/765,063

(22) Filed: Jan. 17, 2001

(65) Prior Publication Data

US 2003/0233041 A1    Dec. 18, 2003

(51) Int. Cl.
*A61B 5/05*    (2006.01)
(52) U.S. Cl. ...................... 600/407; 324/692
(58) Field of Classification Search ............... 600/407, 600/409, 547; 346/141; 340/573.3; 324/228, 324/244, 254, 692
See application file for complete search history.

(56) References Cited

U.S. PATENT DOCUMENTS

| 4,007,420 | A | * | 2/1977 | Halek et al. ................ 346/141 |
| 4,688,580 | A | * | 8/1987 | Ko et al. .................... 600/547 |
| 4,968,974 | A | * | 11/1990 | Sakano .................... 340/573.3 |
| 5,458,142 | A | * | 10/1995 | Farmer et al. .............. 600/409 |

OTHER PUBLICATIONS

Abbadie, C., et al., "Differential Contribution of the Two Phases of the Formalin Test to the Pattern of c-fos Expression in the Rat Spinal Code: Studies With Remifentanil and Lidocaine", *Pain, 69*, (1997), 101-110.

Abbott, F. V., et al., "The Formalin Test: Scoring Properties of the First and Second Phases of the Pain Response in Rats", *Pain, 60*, (1995),91-102.

Abram, S. E., et al., "Morphine, but not Inhalation Anaesthesia, Blocks Post-Injury Facilitation. The Role of Preemptive Suppression of Afferent Transmission", *Anesthesiology, 78(4)*, (1993), 713-721.

Abram, S. E., et al., "Systemic Lidocaine Blocks Nerve Injury-Induced Hyperalgesia and Nociceptor-Driven Spinal Sensitization in the Rat", *Anesthesiology, 80(2)*, (1994),383-391.

Aloisi, A. M., et al., "Behavioral Effects of Different Intensities of Formalin Pain in Rats", *Physiology & Behavior, 58(3)*, (1995),603-610.

(Continued)

*Primary Examiner*—Brian L. Casler
*Assistant Examiner*—Baisakhi Roy
(74) *Attorney, Agent, or Firm*—Schwegman, Lundberg, Woessner & Kluth, P.A.

(57) ABSTRACT

An apparatus and method for measuring spatial displacement of an animal's paw injected with irritant. This apparatus comprises an electromagnetic detecting assembly having (1) a transmitting oscillator for generating electrical current (2) an electromagnetic transmitter coil coupled to the oscillator for generating an electromagnetic field (3) an electromagnetic receiving coil placed in axial plane directly below the transmitter coil (4) a first, receiving amplifier connected to the receiving coil (5) an amplitude detector connected to the receiving amplifier (6) a second amplifier connected to the amplitude detector (7) a metal object attached to the animal's paw (8) and a cylindrical observation chamber of a diameter not greater than the diameter of the generated magnetic field.

12 Claims, 11 Drawing Sheets

OTHER PUBLICATIONS

Bannon, A. W., et al., "ABT-594 [(R)-5-(2-azetidinyl-methoxy)-2-chloropyridine]: A Novel, Orally Effective Antinociceptive Agent Acting via Neuronal Nictotinic Acetylcholine Receptors: II. In Vivo Characterization", *The Journal of Pharmacology and Experimental Therapeutics*, 285(2), (1998),787-794.

Bhatnagar, S. , et al., "The Effects of Prior Chronic Stress on Cardiovascular Responses to Acute Restraint and Formalin Injection", *Brain Research*, 797, (1998),313-320.

Brennan, T. J., "AMPA/Kainate Receptor Antagonists as Novel Analgesic Agents", *Anesthesiology*, 89(5), (1998), 1049-1051.

Buerkle, H. , et al., "Effect of Continuous Spinal Remifentanil Infusion on Behaviour and Spinal Glutamate Release Evoked by Subcutaneous Formalin in the Rat", *British Journal of Anaesthesia*, 80, (1998),348-353.

Chaplan, S. R., et al., "Efficacy of Spinal NMDA Receptor Antagonism in Formalin Hyperalgesia and Nerve Injury Evoked Allodynia in the Rat", *Journal of Pharmacology and Experimental Therapeutics*, 280(2), (1997),829-838.

Clavelou, P. , et al., "The Orofacial Formalin Test in Rats: Effects of Different Formalin Concentrations", *Pain*, 62, (1995),295-301.

Coderre, T. J., et al., "The Formalin Test: A Validation of the Weighted-Scores Method of Behavioral Pain Rating", *Pain*, 54, (1993),43-50.

Dallel, R. , et al., "Evidence for a Peripheral Origin of the Tonic Nociceptive Response to Subcutanous Formalin", *Pain*, 61, (1995), 11-16.

Dickenson, A. H., et al., "Peripheral Origins and Central Modulation of Subcutaneous Formalin-Induced Activity of Rat Dorsal Horn Neurones", *Neuroscience Letters*, 83, (1987),207-211.

Dickerson, A. H., et al., "Chapter 36 Response Properties of Dorsal Horn Neurons: Pharmacology of the Dorsal Horn", *In: Anesthesia: Biologic Foundations*, Yaksh, T., et al., Editors, Lippincott-Raven Publishers,(1997),611-624.

Dirig, D. M., et al., "Intrathecal Baclofen and Muscimol, but not Midazolam, are Antinociceptive Using the Rat-Formalin Model", *Journal of Pharmacology and Experimental Therapeutics*, 275(1), (1995),219-227.

Dray, A. , et al., "Systemic Capsaicin and Olvanil Reduce the Acute Algogenic and the Late Inflammatory Phase Following Formalin Injection into Rodent Paw", *Pain*, 47, (1991),79-83.

Dubuisson, D. , et al., "The Formalin Test: A Quantitative Study of the Analgesic Effects of Morphine, Meperidine, and Brain Stem Stimulation in Rats and Cats", *Pain*, 4, (1977),161-174.

Handwerker, H. O., "Electrophysiological Mechanisms in Inflammatory Pain", *Agents and Actions. Supplements, 32—Drugs in Inflammation*, (1991),91-99.

Hunter, J. C., et al., "Role of Excitatory Amino Acid Receptors in the Mediation of the Nociceptive Response to Formalin in the Rat", *Neurosci Lett*, 174, (1994),217-221.

Jett, M. F., et al., "The Formalin Test in Rat: Validation of an Automated System", *Pain*, 64, (1996),19-25.

Jourdan, D. , et al., "A New Automated Method of Pain Scoring in the Formalin Test in Rats", *Pain*, 71, (1997),267-270.

Malmberg, A. B., et al., "Antinociceptive Actions of Spinal Nonsteroidal Anti-Inflammatory Agents on the Formalin Test in the Rat", *The Journal of Pharmacology and Experimental Therapeutics*, 263(1), (1992),136-146.

Malmberg, A. B., et al., "Antinociceptive Effect of Spinally Delivered Prostaglandin E Receptor Antagonists in the Formalin Test on the Rat", *Neuroscience Letters*, 173, (1994),193-196.

Malmberg, A. B., et al., "Effect of Continuous Intrathecal Infusion of ω-conopeptides, N-type Calcium-Channel Blockers, on Behavior and Antinociception in the Formalin and Hot-Plate Tests in Rats", *Pain*, 60, (1995),83-90.

Malmberg, A. B., et al., "Pharmacology of the Spinal Action of Ketorolac, Morphine, ST-91, U50588H, and L-PIA on the Formalin Test and an Isobolographic Analysis of the NSAID Interaction", *Anesthesiology*, 79(2), (1993),270-281.

Malmberg, A. B., et al., "Spinal Nitric Oxide Synthesis Inhibition Blocks NMDA-Induced Thermal Hyperalgesia and Produces Antinociception in the Formalin Test in Rats", *Pain*, 54, (1993),291-300.

Nozaki-Taguchi, N. , et al., "A Novel Model of Primary and Secondary Hyperalgesia After Mild Thermal Injury in the Rat", *Neuroscience Letters*, 254, (1998),25-28.

Peterson, M. A., et al., "The Differential Contribution of Capsaicin-Sensitive Afferents to Behavioral and Cardiovascular Measures of Brief and Persistent Nociception and to Fos Expression in the Formalin Test", *Brain Research*, 755(1), (1997),9-16.

Prado, W. A., et al., "Antinociceptive Effect of Intrathecal Neostigmine Evaluated in Rats by Two Different Pain Models", *Brazilian Journal of Medical and Biological Research*, 30, (1887), 1225-1231.

Price, D. D., "Psychophysical Observations on Patients With Neuropathic Pain Relivered by a Sympathetic Block", *Pain*, 36, (1989),273-288.

Puig, S. , et al., "Formalin-Evoked Activity in identified Primary Afferent Fibers: Systemic Lidocaine Suppresses Phase-2 Activity", *Pain*, 64, (1995),345-355.

Raboisson, P. , et al., "Effects of Subcutaneous Formalin on the Activity of Trigeminal Brain Stem Nociceptive Neurones in the Rat", *Journal of Neurophysiology*, 73(2), (1995),496-505.

Shimoyama, N. , et al., "Spinal Gabapentin is Antinociceptive in the Rat Formalin Test", *Neuroscience Letters*, 222(1), (1997),65-67.

Simmons, R. M., et al., "Kainate GluR5 Receptor Subtype Mediates the Nociceptive Response to Formalin in the Rat", *Neuropharmacology*, 37, (1998),25-36.

Singh, L. , et al., "The Antiepileptic Agent Gabapentin (Neurontin) Possesses Anxiolytic-Like and Antinociceptive Actions that are Reversed by D-Serine", *Psychopharmacology*, 127, (1996),1-9.

Tallarida, R. J., et al., *Manual of Pharmacologic Calculations With Computer Programs*, (2nd Edition, 1987, Springer-Verlag New York, Inc.),p. 291.

Taylor, B. K., et al., "Early Nociceptive Events Influence the Temporal Profile, but not the Magnitude, of the Tonic Response to Subcutaneous Formalin: Effects with Remifentanil", *The Journal of Pharmacology and Experimental Therapeutics*, (1997),876-883.

Taylor, B. K., et al., "Persistent Cardiovascular and Behavioral Nociceptive Responses to Subcutaneous Formalin Require Peripheral Nerve Input", *The Journal of Neuroscience*, 15(11), (1995),7575-7584.

Taylor, B. K., et al., "Pituitary-Adrenocortical Responses to Persistent Noxious Stimuli in the Awake Rat: Endogenous Corticosterone Does Not Reduce Nociception in the Formalin Test", *Endocrinology, 139*(5), (1998),2407-2413.

Tjølsen, A. , et al., "The Formalin Test: An Evaluation of the Method", *Pain, 51*, (1992),5-17.

Wheeler-Aceto, H., et al., "Standardization of the Rat Paw Formalin Test for the Evaluation of Analgesics", *Psychopharmacology, 104*, (1991),35-44.

Wheeler-Aceto, H. , et al., "The Rat Paw Formalin Test: Comparison of Noxious Agents", *Pain, 40*, (1990),229-238.

Woolf, C. J., et al., "Long Term Alterations in the Excitability of the Flexion Reflex Produced by Peripheral Tissue Injury in the Chronic Decerebrate Rat", *Pain, 18*, (1984), 325-343.

Yaksh, T. L., et al., "Central Pharmacology of Nociceptive Transmissions", *In: Textbook of Pain*, (4th Edition, Churchill Livingstone),(1999),253-308.

Yaksh, T. L., "Chapter 40 Preclinical Models of Nociception", *In: Anesthesia: Biologic Foundations (vol. 1)*, Yaksh, T. , et al., Editors, Lippincott-Raven Publishers,(1997),685-718.

Yaksh, T. L., "Chronic Catherization of the Spinal Subarachnoid Space", *Physiology & Behavior, 17*, (1976), 1031-1036.

Yaksh, T. L., et al., "Intrathecal Capsaicin Depletes Substance P in the Rat Spinal Cord and Produces Prolonged Thermal Analgesia", *Science, 206*(4417), (1979),481-483.

Yaksh, T. L., et al., "The Spinal Biology in Humans and Animals of Pain States Generated by Persistent Small Afferent Input", *Pro. Natl. Acad. Sci. USA. 96*, (1999),7680-7686.

Yamamoto, T. , et al., "Stereospecific Effects of a Nonpeptidic NK1 Selective Antagonist, CP-96,345: Antinociception in the Absence of Motor Dysfunction", *Life Sciences, 49*(26), (1991),1955-1963.

Yoon, M. H., et al., "The Effect of Intrathecal Gabapentin on Pain Behavior and Hemodynamics on the Formalin Test in the Rat", *Anesthesia and Analgesia, 89*, (1999),434-439.

Zar, J. H., "Table of Contents", *Biostatistical Analysis*, (2nd Edition, 1984, Prentice Hall, Inc.), 134-138.

* cited by examiner

APPARATUS AND METHOD FOR DETECTING FLINCH RESPONSE TO NOCICEPTIVE AGENTS

BACKGROUND OF THE INVENTION

1. Field of the Invention

The present invention concerns detection of response to nociceptive pain. This invention particularly concerns an automated model for screening anti-nociceptive agents by detecting and measuring a flinch response in an animal whose extremity has been subjected to an irritant such as formalin.

2. Description of the Prior Art

The escape response or agitation evoked by a transient, strong stimulus attests to there being a close relationship between stimulus intensity, peripheral afferent discharge and magnitude of the pain state as defined by response latency and magnitude. There are situations, however, in which the magnitude of the response to pain may exceed what would normally be anticipated given the magnitude of the physical stimulus and the afferent traffic generated by that stimulus (31, 45, 47). These situations are loosely considered as reflecting a state of hyperalgesia, possibly arising from sensitization of the peripheral terminal and/or a central facilitation.

Several preclinical models have been developed that may reflect the significance played by such facilitation on behavior. The common characteristic found in these models is the injury that is induced and its causing of the sensory axon to produce a persistent discharge. A frequently used method of producing injury in the rat is the subcutaneous injection of a small volume of irritant such as formalin into its hind paw. Typically, after the formalin injection, the rat displays a biphasic (Phase I and Phase II) incidence of flinching (rapid paw shaking) and licking of the injected paw (18, 42, 43). The behavioral syndrome produced by the injection of formalin into the paw has been widely used to define the pharmacology of systems that regulate facilitated processing. The "formalin test" has evolved into a widely used tool in the screening of analgesic and anti-hyperalgesic drugs (45).

An important limitation of this behavioral model is its labor-intensive nature regarding data collection and the time required to train observers in its reliable implementation. Several automated systems have been proposed to facilitate data collection. One approach has been to employ strain gauges to measure mass movements of a rat in a confined cylindrical cage (21). A second model involves a video system that employs a pattern recognition algorithm (22). Though of merit, these approaches are limited in that each only indirectly measure movement of the injected paw. Therefore, there is a need for an approach that directly measures movement.

This invention addresses this limitation by presenting a system that assesses only the movement of the injected paw. As described below, this approach involves placing a metal band on the injected paw and detecting the movement of that band with a localized low strength sinusoidal electromagnetic field.

SUMMARY OF THE INVENTION

One object of the present invention contemplates the capability of electronically detecting a response to chemically induced nociceptive pain directly.

Another object of the present invention contemplates a method for rapid screening for nociceptive agents, using an automated model.

To achieve these objectives, the most preferred embodiment of this invention is an automated flinch-detection apparatus for measuring spatial displacement of an animal's paw injected with irritant. This apparatus comprises an electromagnetic detecting assembly having (1) a transmitting oscillator for generating electrical current (2) an electromagnetic transmitter coil coupled to the oscillator for generating an electromagnetic field (3) an electromagnetic receiving coil placed in axial plane directly below the transmitter coil (4) a first, receiving amplifier connected to the receiving coil (5) an amplitude detector connected to the receiving amplifier (6) a second amplifier connected to the amplitude detector (7) a metal object attached to the animal's paw (8) and a cylindrical observation chamber of a diameter not greater than the diameter of the generated magnetic field.

The chamber is placed directly over the receiving/transmitting coil assembly, wherein the current generated by the transmitting oscillator circulates in the transmitter coil, creating an electromagnetic field that penetrates the metal object, creating eddy currents perturbing the electromagnetic field. The fluctuating perturbations are picked up by the receiving coil, amplified by the receiving amplifiers detected by the amplitude detector and further amplified, filtered and digitized.

The current passing through the transmitter coil typically generates an electromagnetic field in the 6 to 8 kilohertz range with a signal strength on the order of 5 to 8 milliwatts. The metal object attached to the animal's paw is a small metal annular collar that fits around the paw. The object can also be a small metal "C" collar in incomplete annular form. The metal object can be made of, or contain a ferrous metal. The metal object can also be non-ferrous. The observation chamber is a transparent cylindrical container, insuring that the animal will remain inside the boundaries of the electromagnetic field generated by the coil assembly. The observation chamber may also individual compartments, permitting testing of a plurality of animals The detection assembly below the observation chamber, in this case, would have multiple independent detection units. The observation chamber typically is constructed of any rigid transparent plastic such as, but not limited to, Plexiglas.

Another most preferred embodiment contemplated is a method for measuring a flinch response by an animal whose paw has been subjected to an irritant. This embodiment comprises attaching a metal object to the animal's paw and placing the animal in an observation chamber, as described above, situated directly over a detection assembly having a transmitting oscillator for generating electrical current and an electromagnetic transmitter coil coupled to the oscillator for generating an electromagnetic field. An electrical current is thus generated and received by an electromagnetic receiving coil, which is connected to a receiving amplifier that amplifies the received generated electrical current. An amplitude detector receives the amplified electrical current, which, in turn, is amplified by a second amplifier.

Thus, the current generated by the transmitting oscillator circulates in the transmitter coil, creating an electromagnetic field that penetrates the metal object attached to the animal's paw, creating fluctuating eddy currents perturbing the electromagnetic field. The fluctuating perturbations are picked up by the receiving coil, amplified by the receiving amplifier, and detected by the amplitude detector. The pertubations are further amplified, filtered and digitized to produce a measured response to the applied irritant.

These objects and other aspects and attributes of the present invention will become increasingly clear upon reference to the following drawings and accompanying specification.

Bottom. The graph displays the variation of the magnitude of the magnetic field when in phase with the transmitter current across the bore of the coils using a fixed paw collar configuration. The Y axis presents the dimensionless ratio of "B (magnetic flux density at current location along the radius from coil center)" divided by "B center (magnetic flux density generated at the coil center)" The X axis shows the ratio of flux measured at the specified location along the radius divided by the radius of the receiver (outer) coil. Where the X-axis ratio is 1.0 the measurement is over the receiver coil, In the graph displayed, the transmitter coil is configured to be half the radius of the receiver coil.

Figure 4:
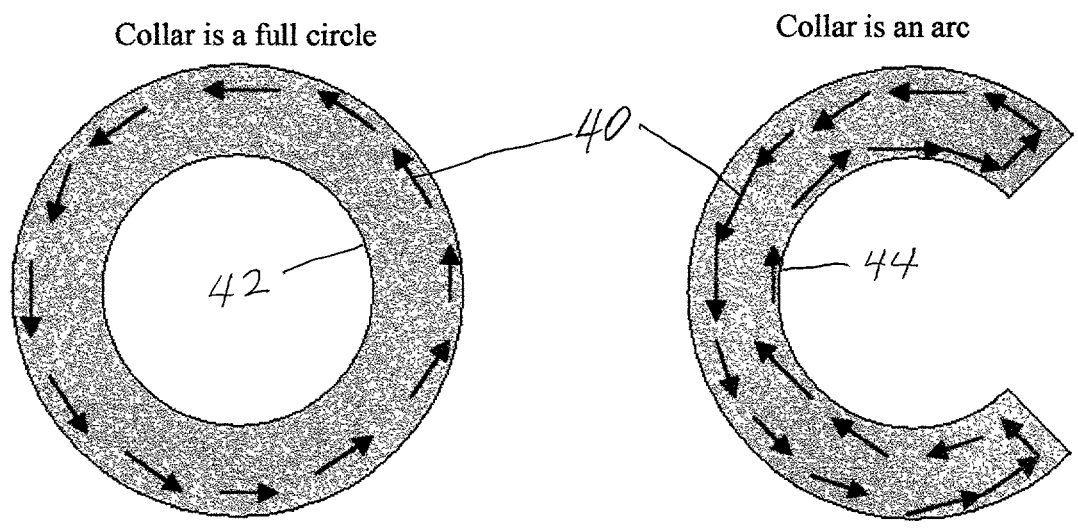

FIG. 4. Representation of current flow occurring with open and closed collar configurations.

Figure 5:
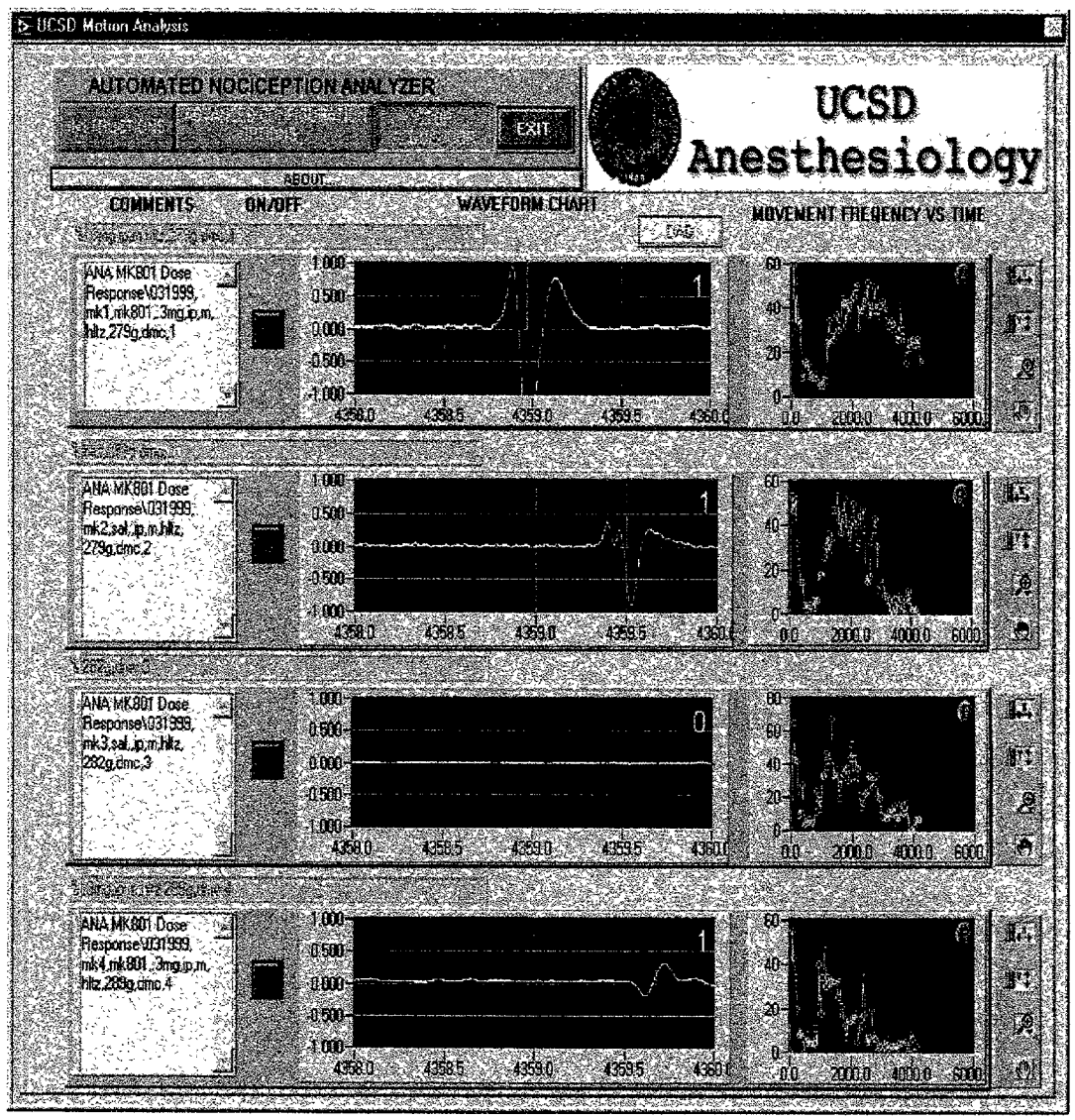

FIG. 5. Photograph displays the screen present during concurrent data collection in 4 rats. The view, for each animal, from left to right is: 1) Study/Animal. 2) The small green virtual "On/Off" switch that initiates and ceases data collection. 3) Smoothed range waveform signal of previous 2 seconds with indicators for flinch activity and flinch count for that interval. 4) Minute by minute flinch count sums over completed portion of the study for each animal.

Figure 6:
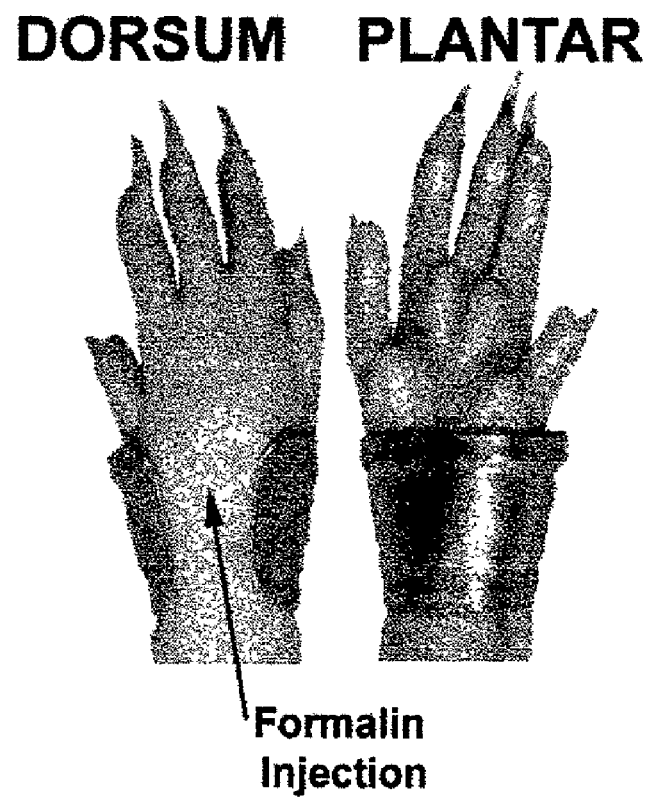

FIG. 6. Drawing indicates the paw band and the typical placement on the left hind paw.

Figure 7:
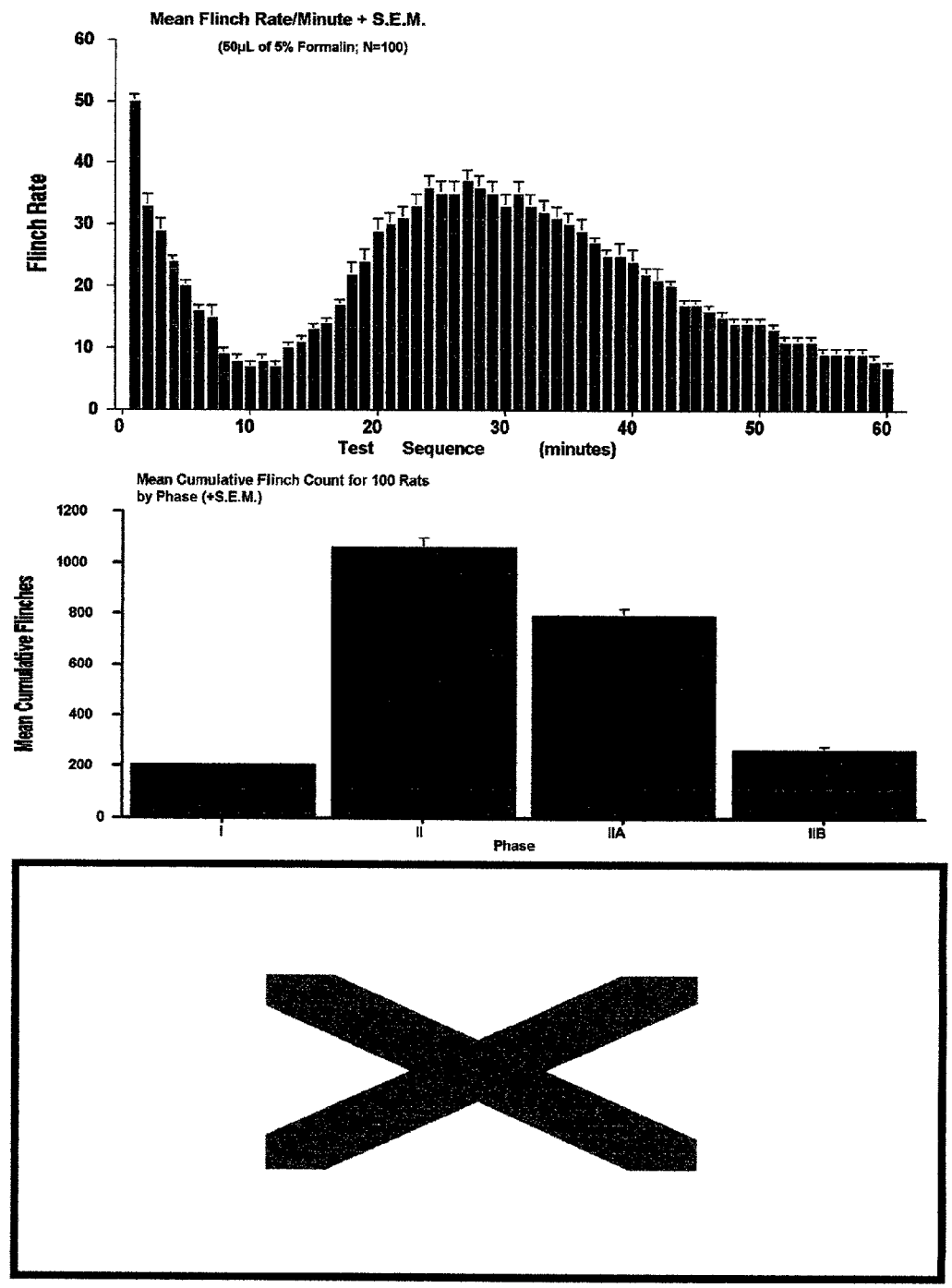

FIG. 7. Top: Average (+SEM) time effect curve for flinching behavior expressed as mean flinches for 100 rats. Middle: Frequency of flinching counts for Phases I and II displayed as a standardized distribution (Z-Scores). Bottom: The mean cumulative flinches (+SEM) observed during Phase I (0–9 minutes), Phase II (10–40 minutes), Phase IIA (10–40 minutes) and Phase IIB (41–60 minutes).

Figure 8:
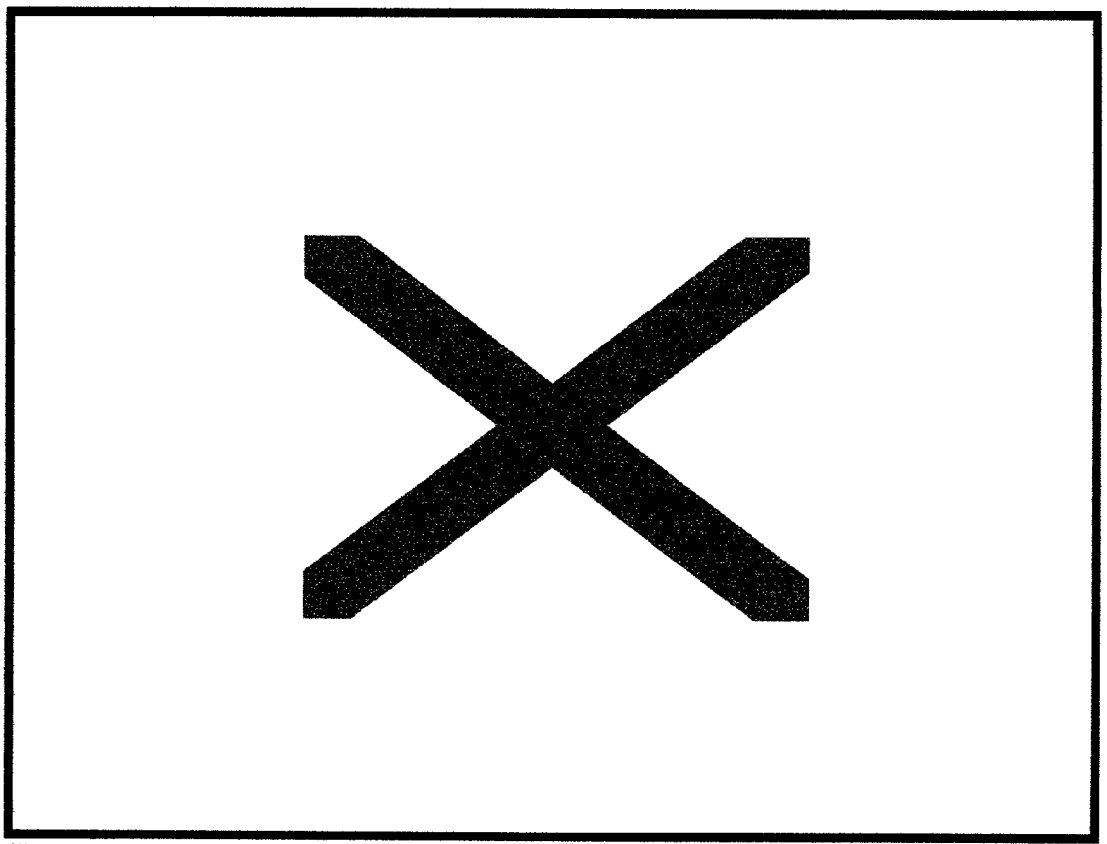

FIG. 8. Control Charts. The Xbar Line Chart provides information about variation between the subgroup means over time by displaying individual group mean flinch counts plotted along its time (Date) axis. The S Line Chart plots subgroup standard deviation along the time axis providing information about variation within the subgroups. Calculated upper and lower control limit (U/LCL) and average (Center) lines have been added.

Figure 9:
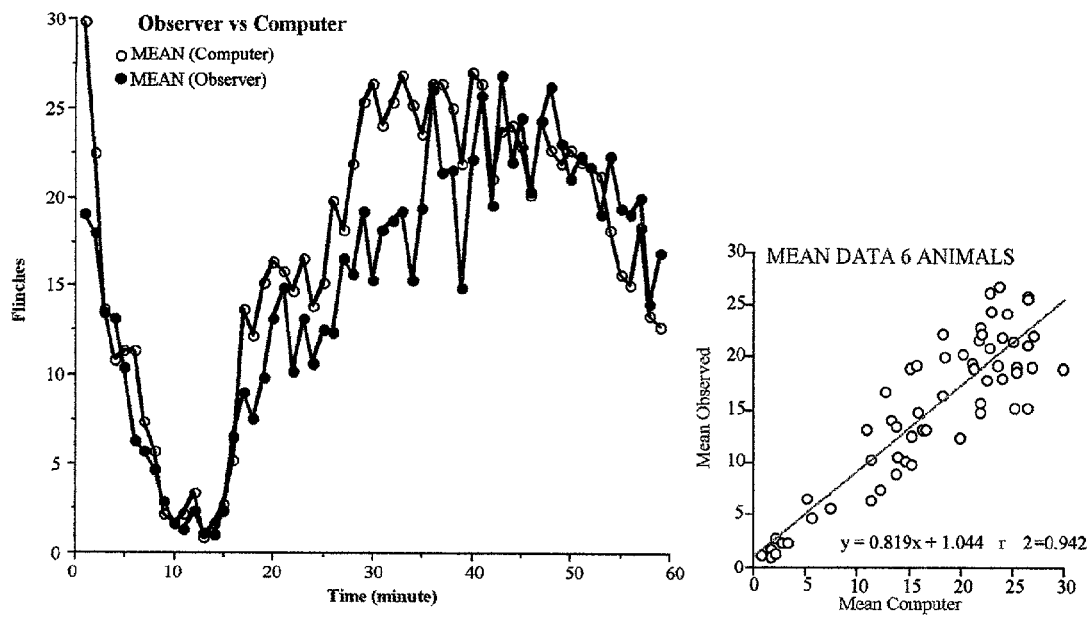

FIG. 9. Time effect plot comparing flinches per minute as determined by a trained human observer and by computer (Left) and a scattergram (Right) showing linear regression between the concurrent human and computer flinch detection of six rats.

Figure 10:
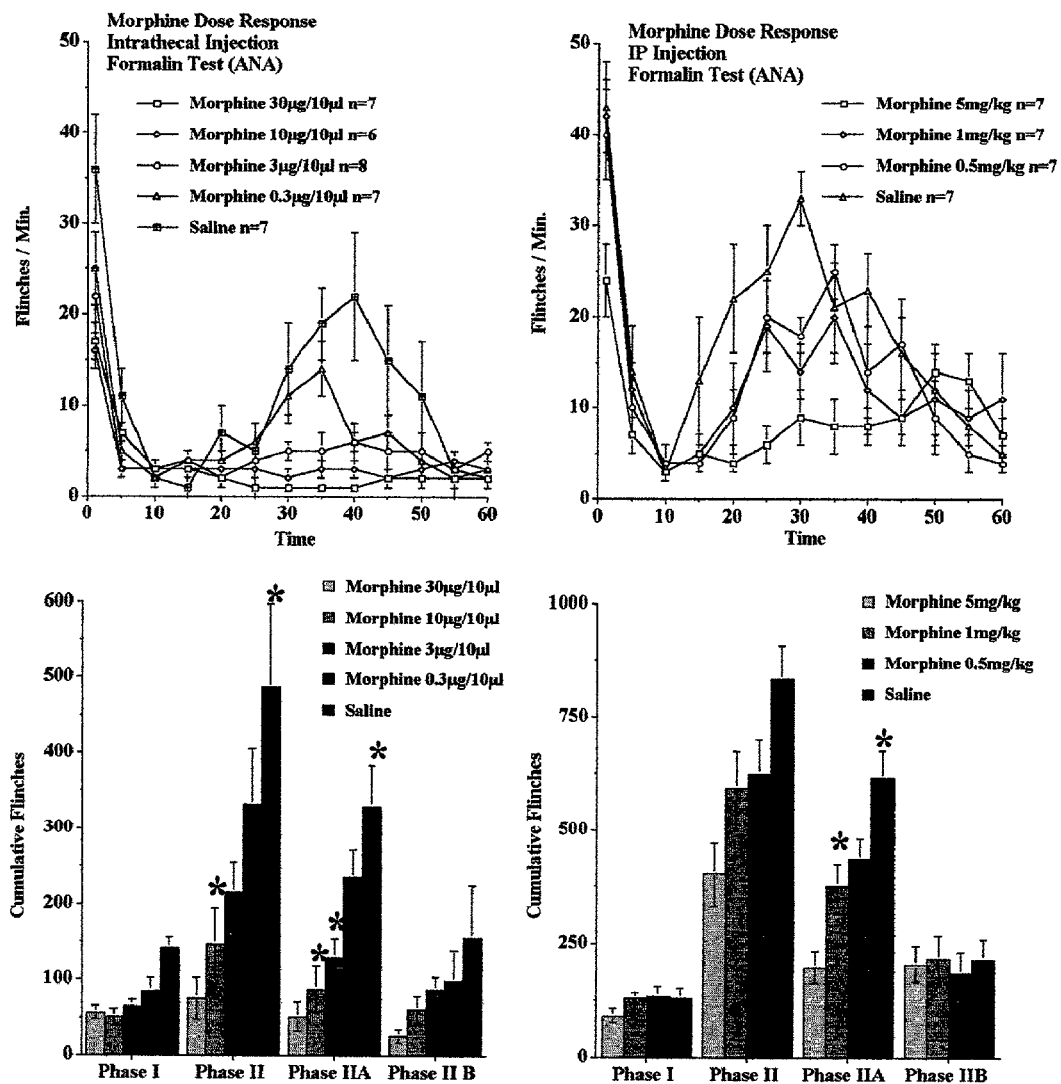

FIG. 10. Time effect curves for vehicle, intrathecal (top left) and intraperitoneal (top right) morphine on formalin induced flinching in the rat. Cumulative flinches, by dose, are presented by phase for intrathecal morphine (bottom left) and for intraperitoneal morphine (bottom right).

*$p<0.05$, 1 Way ANOVA across dose.

Figure 11:
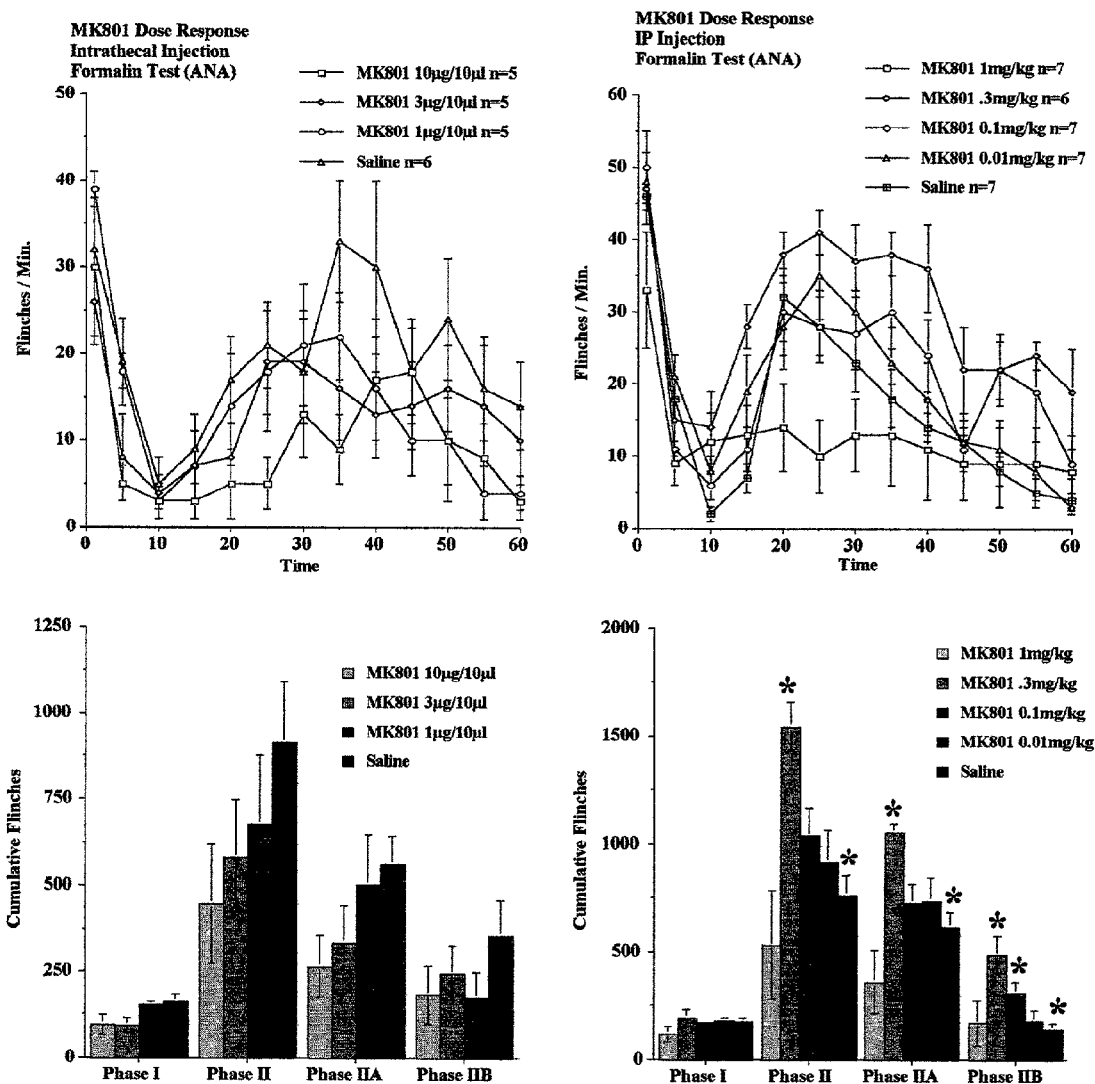

FIG. 11. Time effect curves for vehicle, intrathecal (top left) and intraperitoneal (top right) MK801 on formalin induced flinching in the rat. Cumulative flinches, by dose, are presented by phase for intrathecal MK801 (bottom left) and for intraperitoneal MK801 (bottom right).

*$p<0.05$, 1 Way ANOVA across dose.

DESCRIPTION OF THE PREFERRED EMBODIMENTS

Description of the System.

Figure 1:
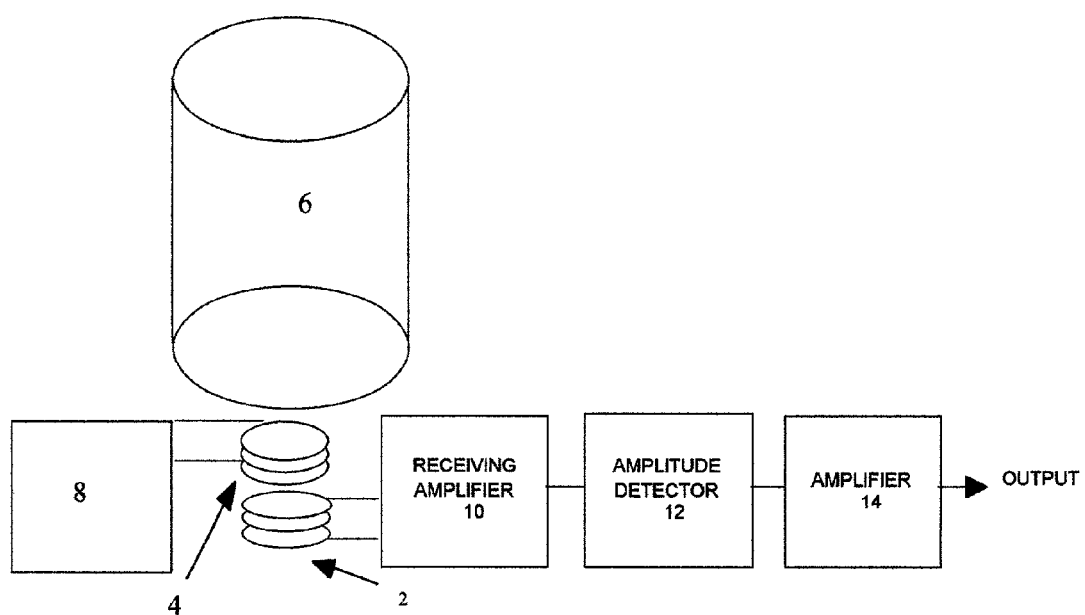
FIG. 1. Top: Block diagram of the detection unit and its functional elements. Bottom: Raw signal tracing over 2 minutes of an animal displaying flinch behavior with arrows added where the processing algorithm detected flinches.
Figure 1:
Figure 2:
FIG. 2. Photograph showing the four detection units in which rats are placed for flinch test and the analog input/ signal processing module. The computer used in flinch detection, display and analysis is located below the testing table.

The detection device consists of a pair of electromagnetic coils as depicted in FIG. 1, one serving as a transmitter 2 and the other as receiver 4. When current passes through the transmitter coil 2, an electromagnetic field in the 6 to 8 kilohertz range is generated with a signal strength on the order of 5 to 8 milliwatts. Eddie currents are set up in ferrous or non-ferrous metals within this field and it is movement of the metal in the field that is detected. Location, size, electrical conductivity and magnetic permeability are factors that determine how well movement of the metal is detected. The receiver coil output is amplified 10–14, filtered and digitized for analysis. The spatial displacement of the injected paw within the electromagnetic field is detected using a small metal collar placed on the paw, as seen in FIG. 6. During testing, the animal is placed into a cylindrical Plexiglas container 6, FIG. 1, (15 cm diameter×30.5 cm high) mounted above the transmitter/receiver coils assembly which is contained within a plastic enclosure. The cylinder 6 insures that the animal (rat) will remain inside the electromagnetic field generated by the coil 2 without the added stress of being in restraint. As shown in FIG. 2, the system includes independent detection units and permits concurrent testing of 4 rats in this case.

Modeling of Physical System Parameters

Several parameters of the electromagnetic field and paw band interaction were initially modeled to understand operating characteristics of the flinch detection system with the aim of defining the contributions of 1) collar permeability; 2) a complete or "O"-shaped collar configuration versus a partial or "C"-shaped collar configuration; and 3) relationship of collar mass and sinusoidal frequency.

Modeling Assumptions.

The following modeling assumptions were made in order to define the effects of the several variables on system performance.

1) While the collar may be variably located and oriented during normal study conditions, for the purpose of this evaluation, the collar was assumed to be centered with respect to the transmitter and receiver coils, thus simplifying the model to an axisymmetric representation of the collar and coils. The coil motion was limited to moving along the coil axis in a vertical direction (see FIG. 3).

2) The collar was considered to be permeable and the representative values were assumed to range from 100 to 1000 (low-grade ferrous) or 100,000 (permalloy). It was assumed that the system contained only materials that could be represented by a single permeability value.

3) Given the dimensions of the coils, the magnitude and the frequency of the voltage (e.g., wavelength relative to coil diameter), the capacitive effect was considered to make a negligible contribution.

4) Motion of the collar was assumed to be limited to height range of between 0.35 and 0.45 inches above and perpendicular to the coils; and periodic, with a period of motion (between 1 and 20 Hz., see below). It is important to note that the field sinusoidal frequency was chosen to be large compared to the target motion (6–9 kilohertz). The extreme positions of 0.35 and 0.45 inches were selected for this modeling to correspond to the elevation extremes of the rat's paw above the coils. Even though the collar is changing its position, this assumption permits the motion of the collar to be treated as a steady state condition. While the direction of motion and coil dimensions will affect the receiver output, the effects due to the collar material, collar thickness and the open vs. intact configuration of the collar can be identified by using a simplified model.

5) For modeling purposes, antennae coils were considered to be of a fixed loop design and constructed of small strands to permit minimal eddy current.

6) The properties of the paw collar (FIG. 4) were varied in terms of its configuration ("C" or "O"), thickness and material permeability. Collar thickness was of interest as it is related to collar weight and the ability of the animal to move freely. Magnetic permeability also was considered to be a significant parameter as it governed whether or not collars were to be made of specialized materials. These factors affect the distribution of the current generated in the collar and its magnetic flux. Collar configuration was important as it related to construction and mounting and distribution of the currents 40 generated within the collar by the transmitter coil. A continuous circle 42 tends to collect maximum current flow along its outer diameter while an incomplete circle 44 (the arc) current distribution loops around the entire surface perimeter as shown in FIG. 4.

6) The electromotive force (EMF), in volts, appearing across the receiver coil is the time derivative of the magnetic flux ($\phi$), in Webers, being linked with the receiver coil of N turns. Since the supply signal is sinusoidal at a frequency (f), in Hertz, the EMF across the receiver coil was computed by the formula $2\pi f N \phi$, where f=8 KHz. Using the assumption that the paw motion can be treated as a steady state problem, the maximum and minimum collar elevations were examined. Electromagnetic analysis, employing the sinusoidal assumption, was performed for each position of the collar. Two solutions were produced: 1) an imaginary solution which represented the electromagnetic field 90° out of phase with the input signal; and 2) the real solution where the electromagnetic field was in phase with the input signal. The peak EMF was computed by combining the EMF for each solution using the square root of the sum of the squares. The effect of collar motion is represented by calculating the differences of EMF at the two extremes of collar position. Calculations were carried out using the commercially available software ANSYS, employing the finite element method to represent the electromagnetic field. Guidelines for analysis of sinusoidal varying fields are provided with the software.

Modeling Results.

The modeling reflects the analysis of four combinations from two collar thicknesses, 0.05 inch and 0.005 inch, and two collar configurations, open and closed circumference. These four cases were evaluated using a variety of magnetic permeability's of the collar (100–100,000) and are summarized in Table 1. The results are normalized by a single case. The values shown represent the relative behavior of the system with respect to alterations in collar design. It is understood that EMF can be also altered by the number of turns in the receiver coil or the transmitter coil and larger paw motions would result in larger values, but the trend, shown by these results, would not be altered.

Figure 3:
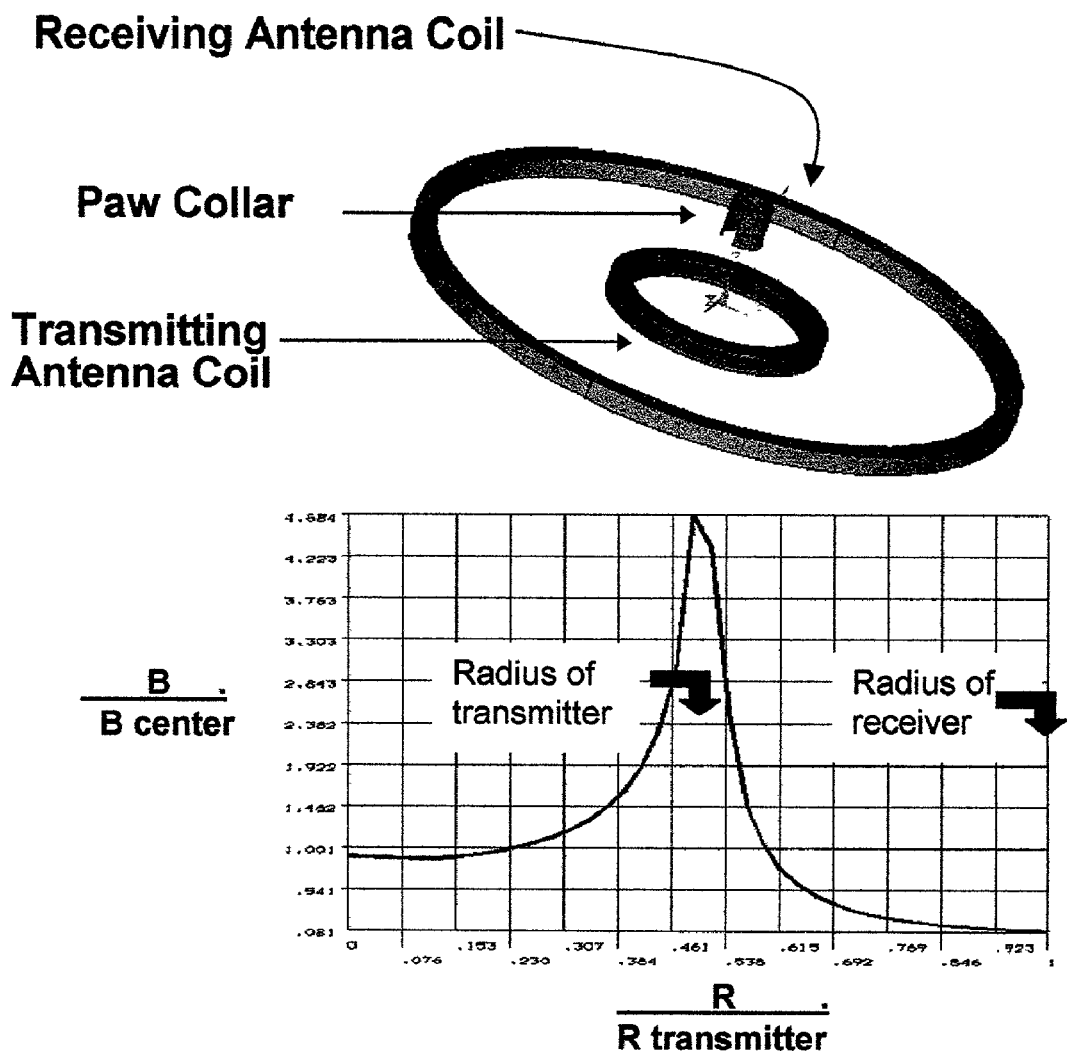
FIG. 3. Top: Displays the modeled transmitter (inner) and receiver (outer) coil configuration and modeled position of the rat paw collar.

As noted above, the data presented in Table 1 reflects the analysis relevant to the paw collar being in the center of the antenna coil. The relative contribution of the several variables would, however, be the same if assessed in any part of the field. To determine the EMF generated across the field, the analysis was carried out for a standard coil across it's radius where the transmitter coil is constructed to be half the radius of the receiver coil. A typical variation of the normalized field across the bore of the transmitter and antenna is shown in FIG. 3. Values larger than unity correspond to the magnetic flux density (B) being larger than the magnetic flux density at the centerline of the coils. This variation is normally observed for such coil configurations. Larger flux densities lead to larger values of EMF since the magnetic flux ($\phi$) is the area integral of the flux density over the bore of the antenna. Collar motion nearer the transmitter radius thus produces larger EMF. Outside the receiver coil, the field is observed to decay rapidly to a level at which a response would not be recorded regardless of the collar design.

TABLE 1

Summary of collar modeling results for voltage signals generated by movement of paw collar in electromagnetic field generated by a surrogate flinch detection device. All EMF receiver values are normalized to Case 2, Permeability of 1,000.

| Permeability | Case 1 (.05", O-shape) | Case 2 (.05", C-shape) | Case 3 (.005", O-shape) | Case 4 (.005", C-shape) |
|---|---|---|---|---|
| 100 | 0.07 | 0.09 | 0.06 | 0.06 |
| 150 | 0.11 | 0.13 | 0.09 | 0.09 |
| 175 | 0.79 | 0.90 | 0.64 | 0.64 |
| 250 | 0.86 | 0.95 | 0.64 | 0.64 |
| 500 | 0.88 | 0.98 | 0.67 | 0.71 |
| 1,000 | 0.95 | 1.00 | 0.69 | 0.76 |
| 100,000 | 1.05 | 1.05 | 0.76 | 0.76 |

Modeling Conclusions.

This analysis provides several conclusions that were of concern during system optimization.

1. The most significant factor was metal permeability. Typical permeability for standard iron is around 1,000. It should also be noted that, if collar cross sectional area is reduced, permeability would be further reduced. The significant drop in the values at a permeability level of 150 and corresponds to the physical conditions of a collar where current cannot be concentrated at its surface. Additional sensitivity could be derived from the use of materials with high permeability and/or with increased thickness. While Cases 3 and 4 show a 20% to 30% decrease in the relative performance, it must be remembered that the mass of the thinner collar is only 10% of the thicker collar.

2. The analysis confirms that use of an open collar does not result in major degradation of system performance.

3. The use of higher permeability materials (>1000) reduces concern with collar geometry.

4. The relationship between frequency of sinusoidal current flow and generated EMF is linear, so increasing energy will increase signal and system sensitivity.

5. Modeling the cross sectional field profile makes clear that the field intensity peaks over the antennae coil. The area to which the animal is restrained should thus be centered over this radius. Importantly, profiling emphasizes the rapid tailing of the flux density as one extends beyond the radius of the receiver coil. This serves to limit the external influences of the field. This, plus the low frequency/energy signal produced by this system reduces the likelihood of EMF interference with other electronic devices.

6. For any given transmitter frequency and energy level, the flux density will be increased by reducing the relative diameter of the transmitter and receiver loops. Thus, the magnitude of the EMF generated for a given paw movement and collar parameter can be increased if enhanced sensitivity is required (e.g., as with a smaller collar or smaller paw displacement).

Signal Analysis

Signal Conditioning.

The analogue signal obtained (FIG. 1) from the receiving coil 2 is filtered at 3 hertz and amplified 10–14 before being digitized at a sampling rate of 1000 Hertz using 12 bit resolution. Beside the flinch behavior that occurs during the testing process, any general displacement of the limb, such as during ambulating and/or grooming activity, also generates signals that need to be addressed. To minimize the interference caused by non-flinch movement, the digitized signal is subjected to real time analysis using a software (LabView) algorithm to pick out a flinch from other paw movement.

Signal Detection.

Two approaches were considered in selection of triggering algorithm. The first employed a "power/frequency" analysis, in which spectral analysis of the limb's flinching movement revealed a characteristic frequency at about 8 Hertz. The peak in the power spectrum was found, however, to be very broad, with significant components observed as low as 1 Hertz and as high as 20 Hertz. The breadth of the flinch bandwidth caused the algorithm to be judged not sufficiently discriminatory at differentiating flinching behavior from regular paw movements.

The second approach was a "zero crossing interval/peak height" analysis based on estimating the amplitude of the signal over a sliding time window. The range of the voltages (maximum-minimum differences) over a moving 128 millisecond interval was calculated to produce a continuous output waveform. This secondary or range waveform contained jagged peaks that correlated well with the flinch transients found in the acquired waveform. It was then smoothed, using a linear convolution filter (a 128 millisecond non-weighted moving average filter), and the smoothed range waveform was examined in real time by a peak detection algorithm set to pick out spikes of ~300 milliseconds duration and amplitudes of >0.5 volts. Each peak thus detected was counted as a paw flinch. This algorithm was observed to produce flinch reports that correlated well with data obtained from animals in which concurrent scoring by trained observers were obtained (see below).

Data Collection

Signal events that meet the criteria of a flinch, as explained above, are captured and summed by time interval (normally set at one-minute increments) over the course of the study. An example of a typical "real time signal showing flinch behavior is displayed in FIG. 1 (bottom). Signals are collected and stored in master raw data spreadsheets by animal according to its Study/Animal identifier. The software (Labview and VisualBasic) presents the data for 4 animals simultaneously on the screen (FIG. 5) and includes for each animal: a) the Study/Animal identifiers including animal numbers, treatment codes, dates and other information relevant to the study; b) a window displaying the previous 2 seconds of digitized signal with markers indicating any flinch detection activity and a count of the flinches within that window; and, c) a line graph of each animal's flinch count by sampling the interval (1 minute) from initiation of testing. A typical view of the computer screen during testing of 4 animals is shown in FIG. 5.

reparation of the Animal

A soft metal band (10 millimeters wide by 27 millimeters long, shaped into a "C", and weighing approximately 0.5 gram) is placed on the hind paw of the animal being tested. The open part of the "C" is positioned at the top of the paw with the arms of the "C" gently compressed to form a bracelet around the paw (see FIG. 6). Retention of the band is enhanced by applying a small amount of adhesive (Cyanoacrylate, Elmers, Columbus, Ohio). The size and weight of the band is sufficiently small so as not to hinder the animal's normal movement. Animals are allowed to accommodate in individual Plexiglas chambers for 1 hour before being moved to a test chamber. Just prior to the animal being placed into the test chamber, it is briefly restrained in a cloth towel, and an irritant (typically 5% formalin, in volumes of 50 $\mu$l) is injected into the dorsum of the banded paw. Data collection is initiated after the animal is placed inside the test chamber.

Drug Delivery

To examine the effects of a drug on flinching behavior, rats received intraperitoneal or intrathecal injections of the drug. Intraperitoneal injections were delivered in volumes of 0.5 ml/kg. Intrathecal injections were done in rats that had been previously implanted with chronic intrathecal catheters (see below) and using drug volumes of 10 $\mu$l followed by a 10 $\mu$l flush using the vehicle.

Drugs/Chemicals

The drugs delivered intrathecally and systemically were morphine sulfate (Malinkrodt) and MK801 (RBI) dissolved in physiological saline (0.9% NaCl w/v). The formalin solutions were prepared by diluting formaldehyde (Fisher Scientific Fair Lawn, N.J., Formalde-Fresh 20%) with physiological saline (0.9% NaCl w/v). Solutions were prepared fresh daily.

Data Analysis

Primary Data Management.

Each animal's flinch count value over an interval of time (usually 1 minute), for the duration of the study (usually 60 minutes), forms the data set used in all subsequent analyses. These data are averaged to characterize similar groups of animals by mean and standard deviation. For graphic display of data, flinches per minute are normally presented; but the mean of the flinches observed over 5 minute time periods (12 per hour) have been used to clarify the graph when a number of groups are being displayed for comparison of time effect. For statistical comparison, the total number of flinches observed during any selected time period (Phase I, II, IIA, IIB) is calculated by accumulating each individual animal's flinches over that time period and averaging the group. Spreadsheet software (EXCEL), used in conjunction with the data collection software, is constructed so as to allow the user to select up to 4 phases within the study's time frame for making phase-related analysis, including phase-cumulative flinch averages, standard deviations, and standard error values, and calculates Per Cent Maximum Possible Effect (% MPE), group means, standard deviations and standard error values when a group of control animals is available. Dose-response curves are based on the calculated % MPE. The flinch time course has frequently been divided into two principal phases: Phase I (0–9 min) and Phase II (10–60 min). In this facility it been observed that different drug effects may arise between early and late Phase II, so, additional analysis occur at Phase IIA (10–40 minutes) and Phase IIB (41–60 minutes) (23). For statistical comparisons, ANOVA is normally carried out between treatment groups for each of the 4 phases, with statistically significance-triggering post hoc test comparisons. Control groups normally consisted of a minimum of 5 rats run in temporal proximity to the drug groups.

Dose Response Analysis.

Dose response slopes and ED50 (effective dose in 50% of animals) values with 95% confidence intervals are calculated using a least squares linear regression analysis carried out on percent inhibition of the cumulative flinching number for each phase (37). The percent inhibition is computed by dividing the response of each animal in a given group by the respective vehicle control group and multiplying by 100.

Statistical Power.

The minimum difference between the flinch count number measured in a test group and that measured in a control group, and determined to be statistically different, was calculated. The calculations were based on data obtained using independent control groups, while assuming different power estimates in the 0.7 to 0.9 range, fixed group sizes (N=8), and where power is defined as 1—the probability of a Type II error being committed. Data were calculated as described elsewhere (52).

System Measurement Stability.

A program was constructed for estimating measurement expectations from the paw flinch system under control conditions, and for documenting long term process reliability. Data was collected at regular intervals over a period of 7 weeks for the purpose of preparing control charts to answer the following quality control issues: a) what is the statistical distribution upon which we can define the process as being "in control," in other words stable and distributed normally; and b) does the process show itself to be "capable", does it meet assigned specification limits. Control and specification parameters (Upper and Lower Control Limits) were defined at study outset to be 3 standard deviations of the generated flinch count distribution for Phases I and II. Analysis was done using the Quality Control Tools found in Statview v.5.0 (SAS Institute Inc. SAS Campus Drive, Cary, N.C. 27513).

The animals were acclimated and then treated only with formalin injection just before the start of the 60 minute data collection period. For each phase, the following values were calculated: a) the Xbar chart Center Line Value, an estimate of the process average and computed by averaging subgroup averages; b) the Xbar chart Control Limits, which identify the distribution range within which the process can be considered in control and computed as 3 times the estimate of the process standard deviation divided by the square root of the subgroup size (n=4); c) the S chart Center Line Value, an estimate of the process variation computed by multiplying an unbiasing constant based upon subgroup size (n=4) by the process standard deviation estimate; d) the S chart Control Limits, which identify the distribution range within which process variation can be considered in control and computed as 3 times the estimate of the process standard deviation times an unbiasing constant based upon the subgroup size (n=4); e) the % Upper and Lower Specification Limits that indicate the number of times the measured values exceeded either the upper or lower control limits and displayed as a % of the total number of measured values; and f) the Capability Index (Cp), an indication of whether the process is in control and can stay within the limits specified as necessary for test relevance, and calculated by dividing the Upper and Lower Specification difference by 6 times the process standard deviation estimate. Upper and Lower Specification limits were calculated by phase as the mean of all tested animals +3 times the standard deviation of the tested population, where, if the Lower Specification limit was less than 0 that limit became 0. A Cp value of greater than 1.33 means that a very small number (6 out of 100,000) of the formalin tests do not fall within the limits considered relevant to the normal testing process (e.g., Cp<1.0, process not capable; Cp=1.0, process marginally capable; Cp>1.0 process is capable).

Animals

Rats were male or female Sprague Dawley, Holtzman (Indianapolis, Ind.). Unless otherwise stated, the typical weight and age of these animals was 275–300 grams and 100–120 days. All animals were given a minimum acclimation period of 3 days on site prior to being entered into a study. For those studies requiring drug to be delivered spinally each rat was implanted with a chronic intrathecal catheter. The catheter, constructed of polyethylene tubing (PE10), was implanted under halothane anesthesia by inserting it intrathecally though the cisternal membrane and passing it 8.5 cm. caudally to the rostral edge of the lumbar enlargement. It was then externalized percutaneously at the top of the head for access during drug delivery (49). Animals receiving intrathecal catheter implants were allowed 4 to 5 days of recovery before testing. No animal showing neural deficit or behavior abnormality was used in the studies. All animals were euthanized immediately after completion of testing.

Study Objectives.

1. Testing for "time of day" and test chamber effects on flinch behavior. Adult groups of male rats (325–375 grams) were tested in the morning (08:00–10:00) or in the afternoon (15:00–17:00) over 5 consecutive days.

2. Testing for process long-term stability. Adult groups (4 rats/group) of male rats (325–375 grams) were tested for flinching behavior over 8 weeks, with separate groups being examined at 3–4 day intervals during this period. Adult groups (4 rats/group) of male rats (325–375 grams) were tested for flinching behavior at 3 groups per week for 4 weeks to evaluate process control and capability using statistical process control analysis. All studies were carried out between 08:00 and 10:00 hours.

3. Testing for body weight effects on flinch behavior. Groups of adult male Holtzman Sprague Dawley rats weighing either 100–125 grams (small), 300–350 grams (medium) or 400–450 grams (large) were tested for flinching behavior. No test, control article or vehicle was given.

4. Test of intrathecal catheterization effect on flinching behavior. Groups of rats were prepared with lumbar intrathecal catheters. After a 5-day recovery period, unimplanted animals of comparable weights (325–350 grams) were tested for formalin response.

5. Test for intrathecal and intraperitoneal drugs on flinch behavior. Groups of rats received intrathecal or intraperitoneal injections of morphine sulfate or MK801. Dose response curves of each agent were generated to relate drug effect to paw flinch and for comparison with previously reported data.

6. Test of correlation between computer and human observer in detecting flinch behavior. A trained observer counted flinches each minute for 60 minutes at the same time as the automated device performed its data logging. A rat was done once in the morning for 6 days.

EXAMPLE 1

Formalin Induced Behavioral Response

The injection of formalin into the dorsum of one hind paw of 100 male Sprague Dawly rats over a period of 10 months showed a reliable biphasic flinching of the injected paw, with peak flinch rates during Phase I and II being on the order of 50 flinches/min and 37 flinches/min. FIG. 7 presents the time course of flinch responses, the mean cumulative flinches observed by Phase (Phase I: 203±9 SEM; II: 1058±39 SEM; IIA: 792±27 SEM; and IIB: 266±16 SEM); and the statistical distribution of flinching in Phase I and II. Analysis of this distribution (Kolmogorov-Smirnov) indicates that each Phase was distributed normally (p>0.9999).

System Stability and Reliability

Separate groups of 4 male Holtzman Sprague Dawley rats were run in the morning (AM) and afternoon (PM) on 5 consecutive days. The following summarizes comparisons of the data.

Comparison Between Test Chambers

There was no difference in the scores for Phase I, II, IIA or IIB generated in each of the 4 chambers when examined over the 5 days of AM and PM testing (Table 2). There were no differences across test chamber for any phase (1-Way ANOVA, p>0.1 to 0.97).

Comparison of Flinching Behaviors Measured over 5 Day Interval

Examination of flinching behavior over 5 consecutive days by phase revealed no systematic differences for Phase I, II, IIA or IIB (Table 3). There were no differences across days for any phase (1-way ANOVA, p>0.07 to 0.32).

TABLE 2

Cumulative flinching behavior (Mean ± SD) by test chamber, by phase.

| GROUP Test Chamber: | N | Phase I | Phase II | Phase IIA | Phase IIB |
|---|---|---|---|---|---|
| 1 | 10 | 93 ± 47 | 794 ± 332 | 584 ± 215 | 210 ± 156 |
| 2 | 10 | 140 ± 35 | 740 ± 192 | 548 ± 134 | 192 ± 91 |
| 3 | 10 | 151 ± 64 | 692 ± 331 | 508 ± 208 | 184 ± 149 |
| 4 | 10 | 131 ± 65 | 737 ± 162 | 542 ± 107 | 195 ± 79 |

Paw Flinch System Stability Measurements

Table 4 shows the results of the initial data analysis taken on selected days using 4 animals per day over a period of 7 weeks. For both Phase I and Phase II the following values were calculated: a) the Xbar chart Center Line value, an estimate of the process average; b) the Xbar chart Control Limits, which identify the distribution range within which the process; c) the S chart Center Line Value, an estimate of the process variation; d) the S chart Control Limits, which identify the distribution range within which process variation can be considered in "control"; e) the % Upper and Lower Specification Limits (% U/L SL) indicating the number of times the measured values exceeded either upper or lower control limits and displayed as a % of the total number of tests run; and f) the

TABLE 3

Cumulative flinching (Mean ± SD) observed over 5 consecutive days, by phase.

| GROUP | N | Phase I | Phase II | Phase IIA | Phase IIB |
|---|---|---|---|---|---|
| Day 1 | 8 | 133 ± 56 | 660 ± 175 | 522 ± 106 | 138 ± 106 |
| Day 2 | 8 | 103 ± 59 | 620 ± 187 | 449 ± 93 | 171 ± 111 |
| Day 3 | 8 | 150 ± 60 | 889 ± 401 | 658 ± 234 | 231 ± 169 |
| Day 4 | 8 | 149 ± 61 | 860 ± 175 | 609 ± 139 | 251 ± 73 |
| Day 5 | 8 | 109 ± 42 | 676 ± 208 | 491 ± 171 | 186 ± 110 |

Capability Index (Cp), an indication of whether the formalin testing process was in "control" and capable" of staying within the limits specified.

TABLE 4

Paw flinch system stability summary

| GROUP | Xbar Center Value | Xbar Control Limits | S Center Value | S Control Limits | USL | LSL | % > USL | % < LSL | Cp |
|---|---|---|---|---|---|---|---|---|---|
| Phase I | 257 | ±96 | 59 | ±74 | 456 | 50 | 0.0 | 0.0 | 1.064 |
| Phase II | 1298 | ±447 | 274 | ±348 | 2186 | 353 | 0.0 | 0.0 | 1.026 |

EXAMPLE 2

Characterization of the Variables Influencing the Formalin Response

Morning (AM) Versus Afternoon (PM) Test Periods.

Examination of flinching behavior in the morning (08:00–10:00) and in the afternoon (15:00–17:00) over 5 days of testing showed no difference between AM and PM for all four phases (Table 5). There were no differences across time of day for any phase (1-way ANOVA, p>0.10 to 0.99).

TABLE 5

Cumulative flinching behavior (Mean ± SD) as a function of testing time, by phase.

| GROUP | N | Phase I | Phase II | Phase IIA | Phase IIB |
|---|---|---|---|---|---|
| AM | 20 | 129 ± 55 | 684 ± 210 | 506 ± 141 | 179 ± 103 |
| PM | 20 | 129 ± 60 | 797 ± 293 | 586 ± 186 | 212 ± 134 |

Effects of Body Weight on Flinching Behavior.

Three groups of rats differing in body weight (125–175 grams, 300–350 grams and 400–450 grams) were examined for flinching behavior. No difference in flinch response was observed in Phase I, II and IIA (1-way ANOVA, p>0.05). A weight-related difference was seen in the flinching behavior for Phase IIB (1-way ANOVA, p<0.05) (Table 6).

TABLE 6

Cumulative flinching behavior (Mean ± SD) as a function of body weight, by phase.

| GROUP | N | Phase I# | Phase II# | Phase IIA# | Phase IIB* |
|---|---|---|---|---|---|
| 125–175 grams | 8 | 193 ± 45 | 768 ± 208 | 686 ± 174 | 81 ± 69 |
| 300–350 grams | 8 | 133 ± 56 | 660 ± 175 | 522 ± 106 | 138 ± 106 |
| 400–450 grams | 8 | 232 ± 60 | 905 ± 196 | 689 ± 162 | 216 ± 96 | p > 0.05 and *p < 0.05, 1-way ANOVA

Effects of Gender on Flinching Behavior.

Gender differences in flinching behavior was tested using 125–150 gram Holtzman Sprague Dawley rats. No difference in flinch response was observed in Phase I, II and IIA (1-way ANOVA, p>0.05). A gender related difference was seen in the flinching behavior for Phase IIB (1-way ANOVA, p<0.05). (Table 6.)

TABLE 7

Cumulative flinching behavior (Mean ± SD) as a function of gender, by phase.

| GROUP | N | Phase I[#] | Phase II[#] | Phase IIA[#] | Phase IIB* |
|---|---|---|---|---|---|
| Female | 7 | 161 ± 83 | 865 ± 262 | 675 ± 168 | 191 ± 111 |
| Male | 8 | 193 ± 45 | 768 ± 208 | 686 ± 174 | 81 ± 69 |

[#]p > 0.05 and *p < 0.05, 1-way ANOVA

TABLE 8

Cumulative flinching behavior (Mean ± SD) as a function of injection dose, by phase.

| GROUP | N | Phase I | Phase II | Phase IIA | Phase IIB |
|---|---|---|---|---|---|
| No Injection | 8 | 92 ± 56 | 146 ± 102 | 92 ± 48 | 54 ± 79 |
| Saline | 12 | 109 ± 75 | 302 ± 175 | 201 ± 123 | 102 ± 73 |
| Formalin, 0.5% | 12 | 127 ± 66 | 400 ± 185 | 301 ± 169 | 100 ± 79 |
| Formalin, 1.0% | 12 | 171 ± 55 | 613 ± 265 | 495 ± 211 | 118 ± 100 |
| Formalin, 2.5% | 12 | 214 ± 75 | 898 ± 266 | 662 ± 210 | 236 ± 148 |
| Formalin, 5.0% | 12 | 230 ± 84 | 811 ± 194 | 659 ± 131 | 152 ± 88 |

Effect of Formalin Concentrations.

The injection of saline into the paw resulted in a modest incidence of flinching behavior while formalin concentrations from 0.5%/50 µL to 5.0%/50 µL resulted in a concentration-related increase in flinching behavior measured in all phases and as compared to saline (Table 8) (1-way ANOVA, p<0.002). Post hoc analysis between groups disclosed phase and concentration differences in flinch response (Table 9).

Effects of Intrathecal Catheterization on Flinching Behavior

No statistically significant differences were observed in flinch response between animal groups with and without intrathecal catheters over all 4 study phases (1-way ANOVA, p>0.2). (See Table 10)

Comparison Between Computer and Human Observer

On different days 6 male Holtzman Sprague Dawley rats (300–350 grams) were injected with 50 µL of 5% formalin and an experienced human observer counted flinching behavior concurrent with signal acquisition and flinch detection by computer. Phase I counts were observed to be lower for the human observer but

TABLE 9

Post hoc group comparisons of formalin injection concentrations, by phase.

| GROUP COMPARISONS | Phase I | Phase II | Phase IIA | Phase IIB |
|---|---|---|---|---|
| No Injection vs. Saline | — | — | — | — |
| No Injection vs. Formalin, 0.5% | — | — | — | — |
| No Injection vs. Formalin, 1.0% | — | S | S | — |
| No Injection vs. Formalin, 2.5% | S | S | S | S |
| No Injection vs. Formalin, 5.0% | S | S | S | — |
| Saline vs. Formalin, 0.5% | — | — | — | — |
| Saline vs. Formalin, 1.0% | S | S | — | — |
| Saline vs. Formalin, 2.5% | S | S | S | S |
| Saline vs. Formalin, 5.0% | S | S | S | — |
| Formalin, 0.5% vs. Formalin, 1.0% | — | — | — | — |
| Formalin, 0.5% vs. Formalin, 2.5% | S | S | S | S |
| Formalin, 0.5% vs. Formalin, 5.0% | S | S | S | — |
| Formalin, 1.0% vs. Formalin, 2.5% | — | S | — | — |
| Formalin, 1.0% vs. Formalin, 5.0% | — | — | — | — |
| Formalin, 2.5% vs. Formalin, 5.0% | — | — | — | — |

S = Significant difference between groups, p < 0.05, Tukey/Kramer post hoc test.

TABLE 10

Cumulative flinching behavior (Mean ± SD) as a function of catheter, by phase.

| GROUP | N | Phase I | Phase II | Phase IIA | Phase IIB |
|---|---|---|---|---|---|
| Catheterized | 12 | 153 ± 42 | 701 ± 409 | 445 ± 202 | 255 ± 226 |
| Not catheterized | 12 | 129 ± 57 | 741 ± 258 | 546 ± 168 | 195 ± 119 | total counts remained close between the two methods (FIG. 9). A scattergram plot of simultaneously acquired data revealed good correlation ($r^2=0.94$).

EXAMPLE 3

Effects of Systemic and Spinal Drugs on Formalin Evoked Flinching Behavior

Morphine.

Intrathecal and systemic injection of morphine ($\mu$ opioid agonist) resulted in a potent dose dependent reduction of all phases of the flinching response (FIG. 10). The ED50 values were calculated using least squares linear regression analysis of the dose effect (% Maximum Possible Effect, % MPE) curves (Table 11).

MK801. Intrathecal and systemic injection of MK801 (a noncompetitive NMDA receptor antagonist) resulted in a potent dose dependent reduction in Phase II but not Phase I of the flinching response (FIG. 11). The ED50 values were calculated using a least squares linear regression analysis of the dose effect (% Maximum Possible Effect, % MPE) curves (Table 11).

TABLE 11

ED50 values for the effects of systemic morphine, intrathecal morphine and MK801 on flinching behavior (Mean and 95% confidence intervals)*

| GROUP | Phase II | Phase IIA |
|---|---|---|
| IT Morphine (µg) | 1.6 (0.6–4.7) | 1.5 (0.6–3.6) |
| IP Morphine (mg) | 4.7 (7888-.003) | 1.8 (1.1–2.9) |
| IT MK801 (µg) | 9.5 (87-1.0) | 7.3 (43-1.2) |

*Data for IP MK801 were not calculated from dose effect curves due to lack of monotonic sequence.

Power Analysis

The difference in flinch counts necessary to show statistical significance was determined using the following assumptions: a) 2 groups being compared with 8 animals per group; b) a two-tailed analysis; c) a 0.05 level of rejection; and d) a reasonably high probability (70% to 90%) of detecting true group mean differences. Determinations were based on mean and standard deviation averages were derived from 5 different 8-animal formalin control studies (Table 12).

EXAMPLE 4

Injection of formalin into the paw leads to a biphasic flinching behavior with the magnitude of the behavior positively covaried with the concentration of formalin.

TABLE 12

Test Group mean values (X) with the power[#] (70%–90% probability) of showing statistical significance from Control means, by phase, and expressed as a percent of the Control mean and as a range of applicable values. N = 8, p = 0.05, two-tailed.

| GROUP | Control Mean | Control Standard Deviation | Difference*, as % & bounds, for 70% Power | Difference, as % & bounds, for 80% Power | Difference, as % & bounds, for 90% Power |
|---|---|---|---|---|---|
| Phase I | 129 | 56 | 42%, 75 > X > 183 | 47%, 69 > X > 189 | 52%, 62 > X > 196 |
| Phase II | 741 | 229 | 30%, 521 > X > 961 | 33%, 496 > X > 986 | 37%, 466 > X > 1016 |
| Phase IIA | 546 | 149 | 26%, 403 > X > 689 | 29%, 387 > X > 705 | 33%, 367 > X > 725 |
| Phase IIB | 195 | 114 | 56%, 85 > X > 305 | 63%, 73 > X > 317 | 70%, 58 > X > 332 |

[#]Power is 1 - probability of committing a Type II error.
*Minimum detectable difference analysis from BiostatisticalAnalysis, Zar, 1984.

Formalin-Evoked Flinching: Supraspinally Organized Complex Behavior

From the perspective of a model of nociceptive transmission, an important question is whether the formalin-evoked flinching behavior reflects an endpoint that is mediated through the exaggeration of spinal traffic to supraspinal centers, or does the biphasic (Phases I and II) flinching behavior represent an exaggerated spinal reflex? Several observations are relevant. First, injection of formalin induces a variety of complex, unconditioned behaviors, such as licking and guarding of the injected paw, which are reflective of a higher order motor organization. Second, spinal transections markedly reduce Phase I flexion-extension of the formalin injected hind paw and Phase II is abolished (42). Third, in addition to the paw withdrawal, formalin injection induces biphasic autonomic (cardiovascular) and supraspinally mediated hormonal responses (29, 38, 51). Fourth, assessment of the firing patterns of dorsal horn wide dynamic range neurons, many of which are projection neurons, has shown that comparable formalin injections results in a similar biphasic activation pattern (15, 33) and an increase in the expression of cFOS in dorsal horn neurons (1). Jointly, these findings support the argument that Phase II behaviors reflect augmented responses to spinofugal traffic and not simply an augmented reflex.

Role of Small Afferents in Formalin Evoked Flinching.

The flinch response is evoked and maintained by persistent small afferent input. Two lines of evidence support this hypothesized mechanism: i) treatment with the C-fiber neurotoxin capsaicin reduces the response to an irritant injected into the paw, suggesting a role for small afferents (17, 29, 46); and ii) local anesthetic blockade of the afferent input during Phase II reduces dorsal horn neuron activity (15) and halts flinching and grooming (13, 39) during Phase I and Phase II. In other words, all flinching behavior (Phase I and Phase II) requires ongoing afferent traffic.

Mechanisms Underlying the Biphasic Components of the Flinching Behavior

Measurement of the firing pattern of small sensory afferents evoked by formalin injected into their receptive fields reveals an acute burst of activity that persists for several minutes. This initial discharge is followed by a persistent low level of afferent activity in slow (small diameter) and fast (large diameter) sensory afferents (32). Temporally, the initial intense flinching (Phase I; 0–10 min) correlates with the initial afferent barrage, while the prominent second phase of flinching (Phase II: 20–60 min) corresponds with the interval when there is a relatively modest, but nonzero level, of afferent input. An important question is, given that there is reduced afferent traffic during Phase II (32), what is the origin of the prominent flinching that is observed during Phase II? We believe that the system is unexpectedly complex, involving several potential mechanisms, all of which may contribute to this second phase.

Peripheral Components.

As noted above, based on local anesthetic blockade, ongoing afferent traffic is essential for dorsal horn neuron activity and the delayed onset of behavior during the second phase after formalin. Peripheral inflammation generated by formalin can initiate activity, perhaps in populations of small cutaneous afferents that are not normally active and have the ability to strongly drive dorsal horn neurons ("silent nociceptors") (19). This provides a peripheral mechanism that would initiate enhanced neuronal activity and flinching behavior in the face of an apparent reduction in overall afferent traffic during the second phase (13).

Central Components.

Persistent small afferent input evokes a facilitation of spinal nociceptive processing (14, 44). Accordingly, it is reasonable to conclude that intradermal formalin may initiate such a cascade, leading to a state of central facilitation that is maintained during the low level of afferent traffic in Phase II. Such a facilitated state, combined with a low level of ongoing afferent traffic, would provide a mechanism for the observed high level of flinching during Phase I (14). Two observations support this role of a central sensitization: i) delivery of agents believed to suppress small afferent input (e.g., opiates) reduces the Phase II response, even when their action is limited to the interval of Phase I (3, 9), but see studies with systemic opiates (40); and ii) delivery of classes of agents that do not block acute excitation or acute pain behavior, but block afferent-evoked spinal facilitation such as NMDA antagonists, COX inhibitor and NOS inhibitors, diminish the second phase of the formalin-evoked behavior (see Yaksh, 1997 (45) for references).

Interactive Contributions.

It is believed that it is likely that changes in both afferent traffic (peripheral) and spinal processing (central sensitization) components contribute to the observed formalin-induced behavioral states. As noted, sensory afferent recordings have emphasized that formalin injection leads to ongoing activity in large and small afferents. Large afferent activity (e.g. light touch) is not typically associated with the initiation of a pain state. However, after local injury or small afferent activation, an exaggerated response of dorsal horn neurons to high intensity stimuli applied to the site and to low intensity tactile input applied adjacent to the injury site is detected (see Dickenson et al. (14)). These phenomena have the behavioral parallel of 1° hyperalgesia and 2° tactile allodynia (8, 28). Pharmacological studies have shown that the 1° hyperalgesia has a well defined peripheral component, while the 2° tactile allodynia is initiated but not sustained by the primary injury input. We thus hypothesize that the 2nd phase pain behavior may arise from: i) an ongoing central sensitization initiated and maintained by small afferent input; and ii) the afferent traffic coming in from small afferent (normally high threshold) nociceptors) and perhaps of equal importance from large afferents (low threshold, mechanoreceptors) that can induce pain behavior when there is a central sensitization.

Manual Formalin Testing

The evident utility of the formalin response suggests that it serves as a robust model for screening anti-hyperalgesic agents. A limitation is the time and training required to perform the test. In previously published work, the primary behavioral index has been the counting of the number of flinches in which 1 minute flinching epochs are counted every 5 or 10 minutes over a 60 minute observation interval. This spacing of observations permits a single technician to follow several rats concurrently. Other methods, such as the counting of time spent in multiple behaviors (12, 42), might provide additional sensitivity, however, the complexity of such an analysis places limitations on the implementation of the model: i) It reduces in the number of animals that can be followed concurrently; ii) the need for observer vigilance means that with repeated testing during the workday, the drift in operator reliability can surely be anticipated. It is important to note that in work published on the method, such practical issues as reliability between observers over time are not discussed; and iii) the use of indices that involve judgments on weight bearing or appropriate licking behavior requires that the observer undergo extensive training and some form of technique validation to prove that needed skills have been acquired before considering that the data produced is useable. Again, most investigators do not generally discuss these issues. Wheeler-Aceto and Cowan (42) specifically cited the simple counting of formalin flinches as reducing the degree of inter-observer variation. Coderre et al. (12) emphasized the degree of inter-observer reliability but, again, this is likely a best case analysis unencumbered by drug or behavior related perturbation.

Automated Systems

Given the limitations associated with manual assessment of formalin-evoked flinching, efforts have been made to develop automated assessment systems. The systems described include one by Jett and Michaels that involves measurement of mass shifts secondary to the movement of a rat in a confined cylindrical cage (21). The use of a complex filtering algorithm is said to reduce the contribution of whole body movement from those arising from the movement of the much smaller mass of the hind paw. This model has been employed in several reports (7, 29). Another model utilizes a video camera system and relies on pattern recognition. The algorithm employed is not described, but it appears to depend upon the symmetry of the animal (22). In neither case can the movement of the injected paw be defined with certainty. In contrast, the model presented here addresses this issue directly.

Modeling of the Detector System

At the outset, the aim was to minimize radio frequency interference and the interaction of the coil fields with the surrounding environment. Collar size was configured to be unencumbering to the rat and constructed of a metal with sufficient permitivity to generate a useful signal. Modeling of the electromagnetic field and collar interaction was undertaken to determine a workable system configuration and a configuration was defined that uses an open collar to produce a useful signal within a relatively localized field at the frequency range of 6–8 KHz. Computational analysis indicates that increased field strengths can be achieved by using higher coil voltage, or by using a fixed signal strength, and: i) metals of higher permitivity; ii) a higher sinusoidal frequency; and/or iii) increasing field density by decreasing the field coil size.

Validation of the Automated Formalin System

The two methods used here to determine system relevance were: obtaining human and system flinch counts concurrently, and comparing flinch count data obtained from previous drug studies with similar new studies using the automated system.

As indicated, concurrent paw flinch assessment by a trained human observer and by the automated system demonstrated good correlation. There was a tendency for the automatic flinch counts in Phase I to be higher than those obtained by the observer, but this is believed to reflect the inability of the human observer to follow the rapid flinching which is evident during that phase.

With regard to the activity of drugs known to alter flinching behavior, morphine given intrathecally and systemically produced a dose-dependent reduction in all phases of the response to formalin. These results are consistent with the mechanism of action of morphine in which at the spinal level, $\mu$ opiate receptors are believed to diminish the excitability of input associated with the activation of small primary afferents (45). The ED50s obtained from the automated assessment correspond closely with those ED50s reported using human scoring. Intrathecal delivery of an NMDA receptor blocker, MK801, has been shown to block Phase II of the response to formalin and, to a lesser degree, Phase I in a dose-dependent manner. Interestingly, while the intrathecal response curve was clearly monotonic, there was an apparent increase in flinching behavior at the lowest doses after systemic delivery of the drug. Examination of the animals during the study indeed confirmed that there was enhanced activity leading to increases in flinch count. The reason for this biphasic component is not known, but it is appreciated that the non-competitive NMDA antagonists may have stimulatory properties that might reflect a PCP-like action. Such effects may be accounted for if the systemically delivered drug is getting into the brain (as compared to a spinal action).

Assessment of System Reliability

In any assay system, base line stability over time is a primary concern. Baseline flinching behavior was assessed in separate studies over a 5 day, 7 week, and 11 month time increments. Over these intervals there were no statistically significant shifts in baseline activity in standard untreated animals.

A more definite approach is to undertake a statistical process analysis. Using a statistical process control analysis, we specifically focused on the 7 week period. We sought to determine if over the 7 week time increment the process, measurement of paw flinches, was in control (i.e., paw flinch measurement varied only within the limits of a selected statistical distribution) and capable (i.e., a high percentage of the measurements taken fell within previously determined specification limits). A process that is "in control", or stable, can be defined by a normal distribution of the observations obtained over time. One measure of process control is the capability index (Cp). This measure defines how satisfactory a process is at meeting the requirements placed on it. A Cp value of greater than 1.00 means that only a small number of the formalin tests would not fall within the limits considered relevant to the normal testing process. Conversely, a Cp<1.0 indicates that a significant number of observations fell outside of the specified distribution. In the present studies, Cp values for both Phase I and II over a 7 week interval were >1.000 and thus "in control" and "capable".

Though seldom used in behavioral system studies, these types of analyses can: i) bolster confidence in a testing process, ii) help to define its sensitivity limits, and iii) aid in the detection of transient or systematic changes before they affect study results.

EXAMPLE 5

Variables Influence the Formalin Response

Several variables may impact upon the magnitude of the flinching behavior. Using the automated assessment systems, selected variables were examined.

Behavioral Indices.

Injection of formalin into the paw results in a variety of spontaneous behaviors including flinching of the paw, licking of the paw, lifting the paw from the surface of the chamber, changes in weight bearing, and vocalization. Assessment of the intensity of a behavior induced by formalin injection has typically involved one or a combination of measures including the measurement of duration and/or frequency for one or more of the known behaviors (2, 12, 18, 42). In most cases, as formalin concentration increases or as the dose of an analgesic agent (e.g., morphine) decreases, there is a corresponding increase in the assessed index (see references in Table 13). Several authors have demonstrated that weighted measures (e.g., time of licking and flicking) may provide a more robust index with a greater dynamic response at lower formalin concentrations than other simple indices such as flinching. Choice of indices may be influenced by the time required to complete a test and the level of training required to achieve reliability.

Concentration of Formalin.

The current literature indicates that increasing formalin concentration, typically over a range of 0.5 to 5%, leads to a more intense and progressively longer lasting flinch response. Assessment of the intensity of several pain behaviors have shown that as formalin concentration rises, the magnitude or incidence of the measured behaviors, blood pressure or flinching increases (2, 5, 11, 12, 39, 41). In the present studies, we observed a plateau effect such that the maximum was observed at 2.5%. These results, obtained with automated flinch counting, are in accord with previous work using weighted behavioral measures and blood pressure (11, 12, 39).

Rat Strain.

The present studies were done with Sprague Dawly, Holtzman strains. There are few systematic studies describing strain differences with regard to formalin response. A variety of rat strains have been used including Sprague Dawley, Harlan strain (25) and Sprague Dawley, Holtzman strain (see Dirig and Yaksh (16); Wistar (2) and Long Evans (12)). Taylor and colleagues noted that the magnitude of the blood pressure response observed during Phase I was similar in Sprague Dawly rats obtained from two suppliers (Charles Rivers and Bantin Kingman), but that the latter displayed a significantly reduced Phase II response.

Body Weight/Age/Gender

Body weight varies directly with age. In the present work, young (110–125 grams) rats flinched less than larger, older, rats (400–450 grams) of the same strain. There appear to be little differences in flinching behavior as a function of gender. In our work, when matched for size, females and males of a single strain showed comparable flinching behaviors, with the exception of the late component (Phase IIB) in which females showed a statistically greater response than males. The significance of this modest difference is not known.

Catheterization. The surgical placement of a spinal catheter had no significant effect upon flinching behavior as compared to the unimplanted rat been examined for their effects upon Phase II of the formalin test after systemic and intrathecal delivery. Agents may be functionally considered in two classes, those

EXAMPLE 6

Pharmacology of the Formalin Test

The pharmacology of the formalin test has been a subject of considerable investigation. Table 13 summarizes a number of families of agents, which have

TABLE 13

Effects of intrathecal and systemically delivered pharmacological classes of agents on phase II of the formalin test in the rat.

| DRUG | INTRATHECAL | SYSTEMIC |
|---|---|---|
| Agonists | | |
| μ opiate | (25) | (42) |
| ∂ opiate | (25) | |
| K opiate | (25) | (42) |
| Alpha 2 adrenergic | (25) | |
| Adenosine A-1 | (25) | |
| Nicotinic | | (6) |
| GABA A | (16) | |
| GABA-B | (16) | |
| Benzodiazepine | (16) | |
| Gabapentin | (34) | (36) |
| Antagonists | | |
| NMDA antagonist | (10) | (20) |
| Glycine site antag | | (20) |
| Kainate antagonist | | (35) |
| AMPA antagonist | (10) | (20) |
| NK-1 antagonist | (50) | (21) |
| COX inhib | (24) | (24) |
| EP antagonists | (25) | |
| NOS inhibitor | (26) | |
| Sodium ch blocker | | (4) |
| N-Ca ch blocker | (27) | |
| Cholinesterase inihib | (30) | | that will completely reduce Phase II (the facilitated component) and those that appear to exert a significant, but limited, plateau effect. To date, all agents that are effective for acute pain processing fall into the first category and include opiate and alpha 2 agents. Agents which fall in the second category include, for example, NMDA and NK1 receptor antagonists, Adenosine A1 agonists, GABA A/B agonists, and cyclooxygenase inhibitors (47, 48). In this invention, we have demonstrated that the automatic assessment of flinching behavior provides data that are both qualitatively and quantitatively similar to data that has been previously reported by human observers.

CONCLUSIONS

The current literature suggests that the formalin test reflect a neural substrate that involves the generation and support of a facilitated state of processing. This behavior observed during Phase II appears to arise out of the initial barrage of afferent traffic and continuous low-level input found in a formalin-induced injury.

The response of this system is such that it appears to reveal a pharmacology that is considered to reflect facilitated states of processing.

An automated sensing system has been developed that counts the spatial displacement of the injected hind paw. This system has been shown to describe a response count and distribution that resembles that obtained with manual counting systems.

The limitations of this approach are that it only counts paw flinching and does not assess time spent in other behaviors deemed to be representative of the animals pain behavior. Nevertheless, based on sensitivity to formalin concentrations, duration of behavioral responses and response to drugs, there appear to be no distinguishable differences between simple flinch analysis and a weighted behavioral score.

The strength of the system lies in the ability to screen large numbers of animals on a daily basis, absence of operator fatigue, a likely increase in reliability over repeated tests and reduced training time.

In accordance with the preceding explanation, variations and adaptations of the dipolar device for presensing impending cardiac disturbances of the present invention will suggest themselves to a practitioner of the medical instrumentation arts. In the spirit of this invention, these and other possible variations and adaptations of the present invention, and the scope of the invention, should be determined in accordance with the following claims, only, and not solely in accordance with that embodiment within which the invention has been taught.

What is claimed is:

1. An automated flinch-detection apparatus for measuring spatial displacement of an animal's paw injected with irritant, comprising:
   an electromagnetic detecting assembly having
      a transmitting oscillator for generating electrical current;
      an electromagnetic transmitter coil coupled to the oscillator for generating an electromagnetic field;
      an electromagnetic receiving coil placed in a linear plane directly below the transmitter coil; a first, receiving amplifier connected to the receiving coil;
      an amplitude detector connected to the receiving amplifier;
      a second amplifier connected to the amplitude detector;
   a metal object adapted to be attached to the animal's paw; and
   a cylindrical observation chamber of a diameter not greater than the diameter of the generated magnetic field, said chamber placed directly over the receiving/transmitting coil assembly, wherein the current generated by the transmitting oscillator circulates in the transmitter coil, creating an electromagnetic field that penetrates the metal object, creating eddy currents perturbing the electromagnetic field, said fluctuating perturbations being picked up by the receiving coil, amplified by the receiving amplifier, detected by the amplitude detector and further amplified, filtered and digitized to produce a measured spatial displacement of the animal's paw injected with the irritant.

2. The apparatus according to claim 1, wherein the current passing through the transmitter coil generates an electromagnetic field in the 6 to 8 kilohertz range with a signal strength on the order of 5 to 8 milliwatts.

3. The apparatus according to claim 1, wherein the metal object is a small metal annular collar.

4. The apparatus according to claim 1, wherein the metal object is a small metal "C" collar in incomplete annular form.

5. The apparatus according to claim 1, wherein the metal object comprises a ferrous metal.

6. The apparatus according to claim 1, wherein the metal object comprises a non-ferrous metal.

7. The apparatus according to claim 1, wherein the observation chamber is a transparent cylindrical container, insuring that the animal will remain inside the boundaries of the electromagnetic field generated by the coil assembly.

8. The apparatus according to claim 1, wherein the observation chamber has individual compartments permitting testing of a plurality of animals.

9. The apparatus according to claim 1, wherein the detection assembly below the observation chamber has multiple independent detection units.

10. The apparatus according to claim 1, wherein the observation chamber is constructed of any rigid transparent plastic.

11. A method for measuring a flinch response by an animal whose paw has been subjected to an irritant, comprising:
   attaching a metal object to the animal's paw;
   placing the animal in an observation chamber situated directly over a detection assembly having
      a transmitting oscillator for generating electrical current,
      electromagnetic transmitter coil coupled to the oscillator for generating an electromagnetic field;
      an electromagnetic receiving coil that receives the generated electrical current;
      a receiving amplifier that amplifies the received generated electrical current;
      an amplitude detector; and
      an amplifier for amplifying the amplitude detected,
   wherein the current generated by the transmitting oscillator circulates in the transmitter coil, creating an electromagnetic field that penetrates the metal object attached to the animal's paw, creating fluctuating eddy currents perturbing the electromagnetic field,
   wherein said fluctuating perturbations are picked up by the receiving coil, amplified by the receiving amplifier, and detected by the amplitude detector, and wherein said pertubations are further amplified, filtered and digitized to produce a measured spatial displacement of the animal's paw injected with the irritant, measured response to the irritant.

12. A method for measuring a flinch response to pain by an animal whose paw has been subjected to an irritant, comprising:
   attaching a metal object to the animal's paw;
   placing the animal in an observation chamber situated directly over a detection assembly;
   generating electrical current by a transmitting oscillator;
   generating an electromagnetic field by an electromagnetic transmitter coil coupled to the oscillator;
   receiving the generated electromagnetic field by a receiving coil;

amplifying the received generated electrical current by a receiving amplifier having,
an amplitude detector; and
an amplifier for amplifying the amplitude detected,
wherein the current generated by the transmitting oscillator circulates in the transmitter coil, creating an electromagnetic field that penetrates the metal object attached to the animal's paw, creating fluctuating eddy currents perturbing the electromagnetic field,
wherein said fluctuating perturbations are picked up by the receiving coil, amplified by the receiving amplifier, and detected by the amplitude detector, and wherein said perturbations are further amplified, filtered and digitized to produce a measured spatial displacement of the animal's paw injected with the irritant, measured response to the irritant.

* * * * *

UNITED STATES PATENT AND TRADEMARK OFFICE
CERTIFICATE OF CORRECTION

PATENT NO. : 6,996,429 B2  Page 1 of 1
DATED : February 7, 2006
INVENTOR(S) : Yaksh et al.

It is certified that error appears in the above-identified patent and that said Letters Patent is hereby corrected as shown below:

Column 22,
Line 37, insert -- an -- before "electromagnetic".
Line 53, delete "pertubations" and insert -- perturbations --.
Lines 55-56, after "irritant" delete ", measured response to the irritant." and insert -- . --.

Column 24,
Line 6-7, after "irritant" delete ", measured response to the irritant." and insert -- . --.

Signed and Sealed this

Eleventh Day of April, 2006

JON W. DUDAS
*Director of the United States Patent and Trademark Office*